United States Patent [19]

Esanu

[11] 4,073,895
[45] Feb. 14, 1978

[54] ISOPROPYLAMINO PYRIMIDINE ORTHOPHOSPHATE

[75] Inventor: André Esanu, Paris, France

[73] Assignee: Societe d'Etudes de Produits Chimiques, Paris, France

[21] Appl. No.: 769,403

[22] Filed: Feb. 16, 1977

[30] Foreign Application Priority Data

Feb. 18, 1976 United Kingdom ............... 06430/76

[51] Int. Cl.$^2$ .................. A61K 31/505; C07D 239/42
[52] U.S. Cl. .............................. 424/200; 260/256.4 B; 260/256.4 E; 260/256.4 N; 424/251
[58] Field of Search ................. 260/256.4 N, 256.4 B, 260/256.4 E; 424/251, 200

[56] References Cited

U.S. PATENT DOCUMENTS 3,278,536 10/1966 Elslager et al. ............... 260/256.4 B

OTHER PUBLICATIONS

Brown, et al. "Chemical Abstracts," vol. 63, 1965, Col. 16166b.

Primary Examiner—Donald G. Daus
Assistant Examiner—James H. Turnipseed
Attorney, Agent, or Firm—Eyre, Mann, Lucas & Just

[57] ABSTRACT

A therapeutic composition of matter presenting a favorable action in the field of nerve regeneration is disclosed. An effective amount of 2-isopropylamino pyrimidine orthophosphate is incorporated in an appropriate carrier. Also disclosed is a process of producing the orthophosphate of 2-isopropylamino pyrimidine.

2 Claims, No Drawings

ISOPROPYLAMINO PYRIMIDINE ORTHOPHOSPHATE

This invention relates to a new salt of a substituted 2-aminopyrimidine. The new salt is useful as an active agent in medicines for the treatment of neuropathies of various origins, and this invention accordingly provides pharmaceutical preparations containing the salt.

The new salt according to this invention is 2-isopropylaminopyrimidine orthophosphate, which has the formula:

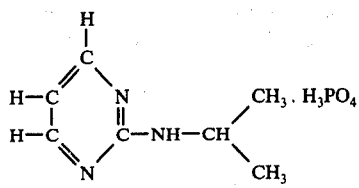

It is a white crystalline powder which melts at 125° C and is soluble in water. Its formula is $C_7H_{14}O_4N_3P$ and its molecular weight is 235.17.

This compound may be obtained according to the invention by reacting 2-isopropylamino-pyrimidine with phosphoric acid, suitably in a solvent for example a lower alcohol.

This invention is illustrated by the following example:

EXAMPLE 6 liters of ethanol and 685 g (5 moles) of 2-isopropylamino pyrimidine were added to a 10 liter reactor and stirred. To the solution were added 600 g (5.2 moles) of phosphoric acid and the mixture was boiled under reflux for one hour. There was obtained a dark green solution which was treated with 30 g of carbon black. After separation and crystallization whilst stirring overnight, the crystallized product was separated, washed with ethanol and dried at 50° C. There was obtained 1,027 g (87% yield) of a white powder melting at 125° C. The analysis of the compound showed a good correspondence with the formula $C_7H_{14}O_4N_3P$.

TOXICITY

The acute toxicity of this compound was determined on mice i.p. and per os and is given in the following table, together with the corresponding values for 2-isopropylamino-pyrimidine dichloroacetate which presents an activity in the same therapeutical field.

|  | L.D. 50 in g/kg | |
|---|---|---|
|  | DICHLOROACETATE | ORTHOPHOSPHATE |
| i.p. | 0.630 | 1.530 |
| per os | 1.700 | 2.830 |

Accordingly the compound of the invention appears far less toxic than this previous compound. The comparison of the subacune toxicities on rats for both compounds confirms a lower toxicity and a better tolerance for this one of the invention.

At similar doses, the following differences between the action of these two salts may be noticed (each experimentation with 10 rats; controls: 10 rats).

| Treatment | Weight Loss Compared To Controls, At 37 th Day | Death At The End Of Treatment |
|---|---|---|
| Dichloroacetate per os 6 days a week for 5 weeks at 570 mg/kg | 23,1 % | 2 |
| Orthophosphate per os 7 days a week for 6 weeks at 600 mg/kg | 7,3 % | 0 |

Moreover an hepatomegalia of 40 to 45% was noticed with dichloroacetate, which was not the case for the orthophosphate of the invention.

PHARMACOLOGY

The pharmacological activity of the compound of the invention may be appreciated from the following comparative experimentation undertaken on the regeneration of the sciatic nerve of the male adult rat (Wistar).

A lesion is made on the sciatic nerve of the rat by a thermosound at −20° C applied 20 minutes on the nerve. The rat is then treated i.p. by the comparison products or by the compound of the invention for a predetermined duration. At the end of the treatment, the rat is killed, the sciatic nerve is separated and placed in contact with a sery at 70 thin parallel platinum wires (interval 1 mm) and an electric signal applied upstream the lesion point is researched on the platinum wires: the more distant wire where the signal can be collected gives the regenerated length.

For each tested composition and each duration of treatment is used a batch of at least 5 rats.

Four compositions have been tested i.p.: the base 2-isopropylaminopyrimidine (87 mg/kg), its dichloroacetate (170 mg/kg, corresponding to 87 mg/kg of the base), its orthophosphate (145 mg/kg, corresponding to 87 mg/kg of the base) and a mixture of vitamins B1 (500 mg/kg), B2 (500 mg/kg) and B6 (5mg/kg) which is known in the art to be the most effective composition in this field. It has been demonstrated that, when using 2-isopropylamino pyrimidine salts, the activity is principally bound with the amount of base actually comprised in the salts, each salt bringing only a slight modification with respect to the base; for that reason, the doses used for dichloroacetate and orthophosphate have been calculated for an equivalence of 87 mg/kg of the base. The interest of the comparison with the base is purely theoretical as the base is not therapeutically administrable (too high pH).

The results of this experimentation are summarized in the following table, together with the figures obtained for control animals (five batches respectively at 7, 11, 14, 17 and 21 days); $m$ indicates the lenght of regenerated nerve as an average value of the lenghts measured for the $n$ animals of the batch. When no figure appear (17 and 21 days) this means that the regenerated lenght exceeded the lenght of the taken sample.

| DURATION (DAYS) |  | 7 | 11 | 14 | 17 | 21 |
|---|---|---|---|---|---|---|
| Controls | m (mm) | 5 | 10,6 | 13,2 | 21,8 | 26,8 |
|  | n | 5 | 5 | 5 | 5 | 5 |
| Base 87 mg/kg | m | 6,3 | 13,8 | 25,1 | — | — |
|  | n | 5 | 6 | 6 | — | — |
| Dichloroacetate (170 mg/kg) (Base 87 mg/kg) | m | 6,5 | 14,5 | 21,1 | — | — |
|  | n | 6 | 6 | 6 |  |  |
| Orthophosphate (145 mg/kg) (Base 87 mg/kg) | m | 6,7 | 16,2 | 22,7 | — | — |
|  | n | 7 | 5 | 7 |  |  |

-continued

| DURATION (DAYS) | | 7 | 11 | 14 | 17 | 21 |
|---|---|---|---|---|---|---|
| B1, B6, B12 | m | 9,4 | 13,2 | 16,2 | 21,4 | 25,5 |
| | n | 5 | 5 | 5 | 5 | 5 |

PRESENTATION — POSOLOGY

This salt can be presented in any therapeutically acceptable form and, for instance, in tablets or in gelatine capsules containing 50 mg per dosage unit together with an excipient such as lactose; for injectable form the product may be dosed in phials containing at least 10 mg of active ingredient dissolved in water. As to the posology for human use, oral administration requires from 250 mg to 2 g per diem whereas injectable form may be administered at doses between 10 mg to 400 mg per diem.

An exemple of the tablet form is given here under:

| | |
|---|---|
| 2-amino pyrimidine orthophosphate | 250 mg |
| Microcrystalline cellulose | 170 mg |
| Corn starch | 115 mg |
| Talc | 47 mg |
| Silicic acid | 6 mg |
| Hydrogenated ricin oil | 5 mg |
| Magnesium stearate | 7 mg |
| | 600 mg |

I claim:
1. The compound 2-isopropylamino pyrimidine orthophosphate.
2. A therapeutic composition of matter presenting a favourable action in the field of the nerve regeneration comprising an effective amount of 2-isopropylamino pyrimidine orthophosphate together with an appropriate carrier.

* * * * *